United States Patent
Izawa et al.

(10) Patent No.: US 8,088,369 B2
(45) Date of Patent: Jan. 3, 2012

(54) ANTI-WRINKLE AGENT

(75) Inventors: Naoki Izawa, Minato-ku (JP); Ryoko Iizuka, Minato-ku (JP); Toshiro Sone, Minato-ku (JP); Katsuyoshi Chiba, Minato-ku (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 337 days.

(21) Appl. No.: 12/377,523

(22) PCT Filed: Aug. 29, 2007

(86) PCT No.: PCT/JP2007/000927
§ 371 (c)(1),
(2), (4) Date: Feb. 13, 2009

(87) PCT Pub. No.: WO2008/026318
PCT Pub. Date: Mar. 6, 2008

(65) Prior Publication Data
US 2010/0291049 A1 Nov. 18, 2010

(30) Foreign Application Priority Data
Aug. 30, 2006 (JP) .................................. 2006-233095

(51) Int. Cl.
*A01N 63/00* (2006.01)

(52) U.S. Cl. .................... 424/93.44; 435/253.4; 514/54; 424/70.13

(58) Field of Classification Search ........................ None
See application file for complete search history.

(56) References Cited

U.S. PATENT DOCUMENTS 5,637,615 A * 6/1997 Yu et al. ........................ 514/557
5,866,146 A 2/1999 Itagaki et al.

FOREIGN PATENT DOCUMENTS

| JP | 62-67028 | | 3/1987 |
| JP | 1992 328083 | * | 8/1992 |
| JP | 7-70209 | | 3/1995 |
| JP | 8-175961 | | 7/1996 |
| JP | 9 2959 | | 1/1997 |
| JP | 9-249524 | | 9/1997 |
| JP | 10-251140 | | 9/1998 |
| JP | 11-228438 | | 8/1999 |
| JP | 11-228439 | | 8/1999 |
| JP | 2002 191387 | | 7/2002 |
| JP | 2005 15446 | | 1/2005 |
| JP | 2007 39423 | | 2/2007 |

OTHER PUBLICATIONS

Marzio et al., J Invest Dermatol, 1999, vol. 113, p. 98-106.*
Yamada et al., 1982, vol. 6, No. 4, Abstract.*
Hiromi Yamada, et al., "Application of a Lactic Acid Bacteria Culture Filtrate to the Skin Care (I) Moisturizing Effect on the Horny Layer", Journal of Japanese Cosmetic Science Society, vol. 6, No. 4, 1982, pp. 238-243 (with English abstract).
Hideo Hosoya, et al., "Use of Culture of Lactic Acid Bacteria in Skin Care Applications (2)—Antioxidative Properties", Journal of Japanese Cosmetic Science Society, Proceedings of the 7th Academic Meeting, 1982, p. 59 (with full English translation).
Minoru Ichioka, et al., "Use of Culture of Lactic Acid Bacteria in Skin Care Applications (3)—Phototoxic Reaction Inhibitory Effect ",Journal of Japanese Cosmetic Science Society, Proceedings of the 8th Academic Meeting, 1983, p. 210 (with full English translation).
Masayuki Kimura, et al., "Use of Culture of Lactic Acid Bacteria (SE) in Skin Care Applications (4)—Effects of SE on Skin Bacterial Flora", Journal of Japanese Cosmetic Science Society, Proceedings of the 9th Academic Meeting, 1984, p. 132 (with full English translation).

* cited by examiner

*Primary Examiner* — Kade Ariani
(74) *Attorney, Agent, or Firm* — Oblon, Spivak, McClelland, Maier & Neustadt, L.L.P.

(57) ABSTRACT

The invention provides an anti-wrinkle agent which has an excellent effect of inhibiting the formation of wrinkles and excellent safeness.
The anti-wrinkle agent contains, as an active ingredient, a culture supernatant of a lactic acid bacterium belonging to *Streptococcus thermophilus*.

8 Claims, 2 Drawing Sheets

Wrinkle depth = d × tanθ

ANTI-WRINKLE AGENT

TECHNICAL FIELD

The present invention relates to a preparation for preventing formation of wrinkles (hereinafter may be referred to as "anti-wrinkle agent"), and more particularly, to an anti-wrinkle agent which exhibits an excellent effect of preventing wrinkle formation on the skin surface caused under irradiation with UV rays.

BACKGROUND ART

Due to aging and external stresses such as temperature, humidity, and UV rays, the skin gradually produces wrinkles and other unfavorable conditions such as rough skin. Previous studies have revealed that hypofunction of fibroblasts in the dermis of the skin and reduction or degradation of the matrix fiber is likely to contribute to the production of wrinkles, etc. To ameliorate such conditions, a variety of means have heretofore been proposed. For example, mention may be given of uses of a loquat (i.e., Japanese medlar) extract (Patent Document 1), oxidized coenzyme A (Patent Document 2), and *Agaricus* mushrooms (Patent Documents 3 and 4). However, those are still not fully satisfactory in terms of wrinkle inhibitory effect and safety.

Meanwhile, it has been reported that a culture supernatant of a lactic acid bacterium; i.e., a culture obtained through inoculating lactic acid bacteria into a medium containing milk as a primarily ingredient, exhibits desirable effects as a skincare preparation for external use. For example, a culture supernatant of a lactic acid bacterium (hereinafter may be referred to as "lactic acid bacterium culture supernatant") has been reported to have a moisturizing effect (Non-Patent Document 1), an antioxidative effect (Non-Patent Document 2), a protective effect against light (Non-Patent Document 3), and a bacterial flora regulating action on the skin and a skin pH control action (Non-Patent Document 4).

Also, in recent years, extensive studies have been conducted on polysaccharides that are produced outside the cells through metabolism of lactic acid bacteria and are contained in a lactic acid bacterium culture supernatant, and thus, many techniques have been reported in relation to external skincare preparations utilizing, as an active ingredient, extracellular polysaccharides produced by various lactic acid bacteria.

Included among such techniques are the use of phosphorylated polysaccharides produced by *Streptococcus lactis, Lactococcus lactis*, or a similar microorganism as a moisturizing agent or a whitening agent (Patent Documents 5 and 6); and the use of polysaccharides produced by a lactic acid bacterium which belongs to the genus *Lactobacillus* as an antiinflammatory agent (Patent Document 7).

These lactic acid bacterium culture supernatants (or extracellular polysaccharides produced by lactic acid bacteria), however, have all been used to produce external skincare preparations whose expected efficacy is moisturizing effect or antioxidative effect, and hitherto, no lactic acid bacterium culture supernatant has been found to be particularly effective in preventing wrinkle formation.

[Patent Document 1] JP-B-1993-17206
[Patent Document 2] JP-A-1996-175961
[Patent Document 3] JP-A-1999-228438
[Patent Document 4] JP-A-1999-228439
[Patent Document 5] JP-A-1998-251140
[Patent Document 6] JP-A-1997-249524
[Patent Document 7] JP-A-1995-70209
[Non-Patent Document 1] Journal of Japanese Cosmetic Science Society, 6(4), p 238, 1982
[Non-Patent Document 2] Journal of Japanese Cosmetic Science Society, Proceedings of the 7th Academic Meeting, 59, 1982
[Non-Patent Document 3] Journal of Japanese Cosmetic Science Society, Proceedings of the 8th Academic Meeting, 210, 1983
[Non-Patent Document 4] Journal of Japanese Cosmetic Science Society, Proceedings of the 9th Academic Meeting, 132, 1984

DISCLOSURE OF THE INVENTION

Problems to be Solved by the Invention

An object of the present invention is to provide a novel skincare preparation for external use (hereinafter referred to as "skin external agent") which exhibits an effect of specifically inhibiting formation of wrinkles on the skin, in particular, wrinkle formation that may be caused by UV irradiation, and which is also very safe to the body.

Means for Solving the Problems

The present inventors have conducted extensive research to solve the above-mentioned problems, and have found that a culture supernatant which is obtained by culturing, among many other lactic acid bacteria, a lactic acid bacterium belonging to *Streptococcus thermophilus* exhibits an excellent effect of specifically inhibiting formation of wrinkles, thereby leading to completion of the invention.

Accordingly, the present invention provides an anti-wrinkle agent which contains, as an active ingredient, a culture supernatant of a lactic acid bacterium belonging to *Streptococcus thermophilus*.

The present invention also provides a method for preventing formation of wrinkles, comprising applying to the skin a composition containing a culture supernatant of a lactic acid bacterium belonging to *Streptococcus thermophilus*.

The present invention also provides use of a composition containing a culture supernatant of a lactic acid bacterium belonging to *Streptococcus thermophilus* as an anti-wrinkle agent.

EFFECTS OF THE INVENTION

Since the anti-wrinkle agent of the present invention contains, as an active ingredient, a culture supernatant obtained through use of a natural lactic acid bacterium, it is very safe to the body and thus can be employed for formulating a variety of external agents for skin care.

BEST MODES FOR CARRYING OUT THE INVENTION

Figure 1:
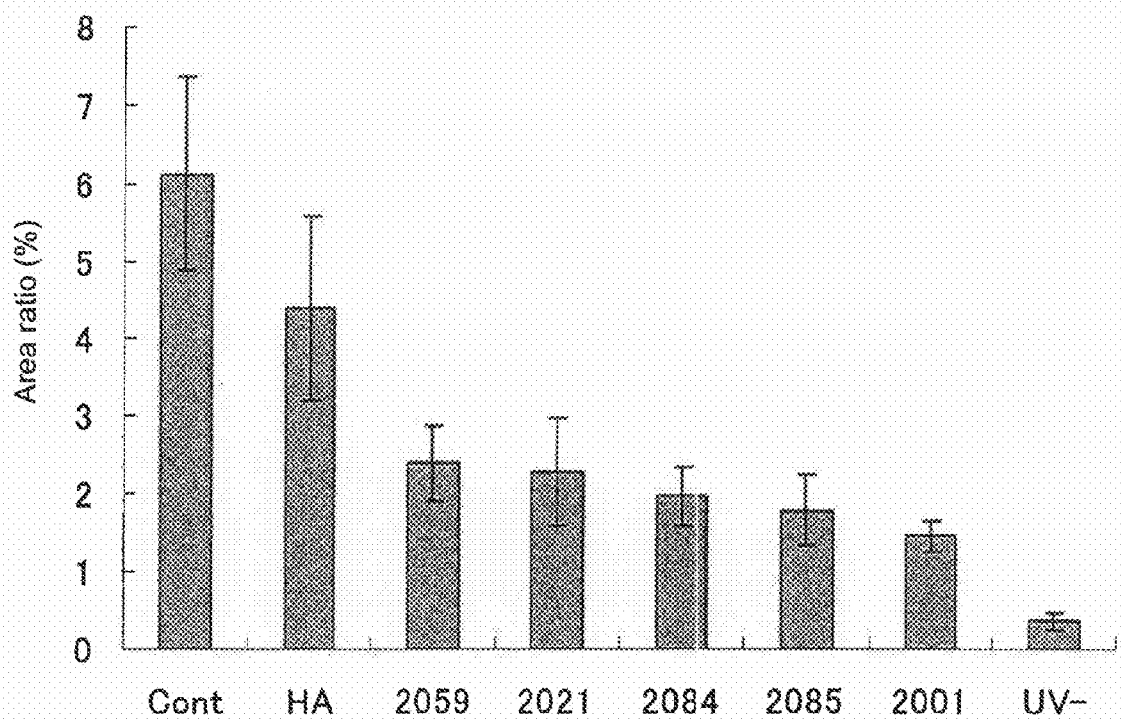
FIG. 1 shows the wrinkle area ratios obtained in Example 1.

The lactic acid bacterium culture supernatant, which is an active ingredient of the anti-wrinkle agent of the present invention, is produced by culturing a lactic acid bacterium belonging to *Streptococcus thermophilus* in a medium containing milk as a main ingredient and removing solid matter from the resultant culture.

No particular limitation is imposed on the lactic acid bacterium belonging to *Streptococcus thermophilus*. However, in order to ensure a sufficient inhibitory effect of a resultant culture supernatant against formation of wrinkles, one member or two or more members selected from the following group are preferably employed: a group consisting of *Streptococcus thermophilus* YIT2021 (FERN BP-7537, deposited on Nov. 1, 1996), *Streptococcus thermophilus* YIT2001 (FERM BP-7538, deposited on Jan. 31, 2001, *Streptococcus thermophilus* YIT2085 (FERN BP-10880, deposited on Aug. 18, 2006), *Streptococcus thermophilus* YIT2084 (FERN BP-10879, deposited on Aug. 18, 2006), and *Streptococcus thermophilus* YIT2059 (FERN BP-10878, Aug. 18, 2006). These lactic acid bacterium strains belonging to *Streptococcus thermophilus* have been deposited with the International Patent Organism Depositary, National Institute of Advanced Industrial Science and Technology (Central 6, 1-1-1 Higashi, Tsukuba-shi, Ibaraki, Japan 305-8566).

Examples of the medium which is preferably employed for culturing a lactic acid bacterium belonging to *Streptococcus thermophilus* include mammal milks such as human milk, cow milk, and goat milk; defatted milk; milk reconstituted from powdered milk or skimmed milk; and dairy products such as cream. Processed soybean products such as soy milk can also be used. Any of these may be used as is to serve as a medium, or alternatively, may be used after being adequately diluted as needed.

Moreover, these media may be supplemented with nutritive ingredients commonly employed in culturing of lactic acid bacteria. Examples of such ingredients include yeast extract; chlorella extract; vitamins such as vitamin A, vitamin B and analogous vitamins, vitamin C, and vitamin E; protein degradation products including a variety of peptides; amino acids; and salts of calcium, magnesium, etc.

Culturing of a lactic acid bacterium belonging to *Streptococcus thermophilus* through use of any of the above-mentioned culture media may be performed following customary methods. Setting of culture temperature and culture period to fall within certain respective ranges is preferred, for the purpose of attaining significant inhibitory effect of the resultant culture supernatant against wrinkle formation. Specifically, when the culture temperature is 30° C. to 45° C., more preferably 37° C. to 42° C., and the culture period is 1 hour to 48 hours, more preferably 4 hours to 24 hours, a culture supernatant exhibiting a remarkable wrinkle-formation inhibitory effect can be obtained. In this case, other culture conditions include maintaining the culture to stand still, stirring, shaking, aerating, etc., from which a suitable technique for culturing may be selected.

The lactic acid bacterium culture supernatant which is used in the present invention can be obtained by subjecting the above-prepared lactic acid bacterium culture to a conventional treatment such as filtering. Prompted by numerous technical findings on extracellular polysaccharides produced by a variety of lactic acid bacteria previously reported in relation to skin external agents, the present inventors performed an analysis of the above-prepared culture supernatants of specified lactic acid bacteria belonging to *Streptococcus thermophilus* for polysaccharides contained therein, and found that the supernatants contain a polysaccharide having glucose, galactose, N-acetylglucosamine, and glucuronic acid. This suggests that the polysaccharide produced by the specified lactic acid bacteria of the invention is a distinct polysaccharide which is different from those polysaccharides produced by known lactic acid bacteria.

An example of a polysaccharide produced by a lactic acid bacterium is hyaluronic acid, which exhibits an excellent moisturizing effect as its typical effect. However, until the present invention was conceived, hyaluronic acid was not known to have an effect of specifically inhibiting wrinkle formation. Similarly, no report has so far been made as to whether polysaccharides produced by other lactic acid bacteria exhibit a wrinkle formation inhibitory effect. The distinct inhibitory effect of the anti-wrinkle agent of the present invention; i.e., the effect of specifically inhibiting formation of wrinkles, is considered to be attributed to a specific structure of a polysaccharide contained in a lactic acid bacterium culture supernatant, which is an active ingredient of the anti-wrinkle agent, wherein the structure has been suggested to be different from that of any polysaccharide produced by previously reported lactic acid bacteria. Therefore, the lactic acid bacterium culture supernatant, which is an active ingredient of the anti-wrinkle agent of the present invention, is clearly distinguished from other lactic acid bacterium culture supernatants that contain a known lactic acid bacterium-produced polysaccharide.

No particular limitation is imposed on the method and manner of use of the anti-wrinkle agent of the present invention, so long as the agent contains, as an active ingredient, a culture supernatant of a lactic acid bacterium belonging to *Streptococcus thermophilus*. Specifically, a culture supernatant of a lactic acid bacterium belonging to *Streptococcus thermophilus* may be used as is, or after concentration or dilution, or as a powder produced by drying through spray drying or freeze drying. Alternatively, a lactic acid bacterium culture, without undergoing any treatment, may directly serve as an ingredient containing the culture supernatant.

The anti-wrinkle agent of the present invention may be formulated into a skincare composition for external use (hereinafter may be referred to as "skin external composition"), such as a cosmetic composition, a pharmaceutical composition, or a quasi-drug composition. Examples of such skincare compositions include basic skincare compositions such as lotions, emulsions, creams, packs, and essences; hair care products such as shampoos, rinses, conditioners, hair lotions, hair liquids, hair creams, and hair milks; bath products such as bath additives; makeup products such as foundations, lipsticks, mascaras, and eye shadows; and special cosmetic products such as sunscreens. No particular limitation is imposed on the amount of the lactic acid bacterium culture supernatant, which functions as an anti-wrinkle agent, incorporated into the above products. The appropriate amount of the supernatant is determined in consideration of, for example, the physical form of the skin external composition. The amount is preferably 0.01 wt. % to 100 wt. %, more preferably 0.1 wt. % to 90 wt. %, even more preferably 1 wt. % to 30 wt. %.

Skin external compositions containing the anti-wrinkle agent of the present invention can be prepared in accordance with a conventional method, and no particular limitations are imposed thereon. For example, the anti-wrinkle agent may be added to pure water, lotion base, cream base, emulsion base, or the like material in a suitable amount that can achieve a desired effect, followed by dissolution or dispersion therein.

The skin external composition may also contain, in addition to the anti-wrinkle agent, which is an essential ingredient, auxiliary substances which are usually incorporated into skin external preparations. Examples of such auxiliary substances include surfactants, oils, alcohols, moisturizers, thickeners, preservatives, antioxidants, chelating agents, pH modifiers, perfumes, colorants, UV absorbers/diffusers, powders, vitamins, amino acids, water-soluble polymers, foaming agents, pigments, plant extracts, animal-derived ingredients, seaweed extracts, pharmaceuticals, additives, and water.

Moreover, since the anti-wrinkle agent of the present invention contains, as its active ingredient, a polysaccharide produced by a lactic acid bacterium which has long been used in foodstuff production, the agent can also be incorporated into a diversified range of foods and beverages. Here, "foods and beverages" mean edible materials that are consumed as functional foods or food materials which are effective for preventing wrinkle formation and which may be taken in the form of the aforementioned anti-wrinkle agent as is, or taken as a lactic acid bacterium culture containing the anti-wrinkle agent, or ingested as food or a beverage containing the anti-wrinkle agent or the lactic acid bacterium culture. For example, suitable auxiliary agents are added to the anti-wrinkle agent, and the mixture is processed with customary means to have a physical shape suited for ingestion; e.g., granules, pills, tablets, capsules, and paste. Alternatively, the anti-wrinkle agent may be added to a variety of foodstuffs including processed meat products such as ham and sausages; processed fishery products such as kamaboko (meatloaf-type product produced from a fish meat paste) and chikuwa (tube-shaped product produced from a fish meat paste); breads; and confectionery products, or may be added to beverages such as water, fruit juice, milk, and soft drinks. Alternatively, a lactic acid bacterium culture containing the anti-wrinkle agent of the present invention may directly serve as a fermented dairy product without being subjected to any additional treatment.

EXAMPLES

The present invention will next be described by way of working examples and test examples. However, the present invention is in no way limited to such examples.

Production Example 1

Preparation of Anti-wrinkle Agent

10% Skimmed milk medium (Difco; 1 mL) was inoculated with cells of *Streptococcus thermophilus* YIT2085 strain (FERM BP-10880), *Streptococcus thermophilus* YIT2021 strain (FERM BP-7537), *Streptococcus thermophilus* YIT2001 strain (FERM BP-7538), *Streptococcus thermophilus* YIT2084 strain (FERM BP-10879), or *Streptococcus thermophilus* YIT2059 strain (FERM BP-10878) in an amount of 1%, followed by culturing for 4 hours at 42° C. Subsequently, the culture was cooled with ice, and trichloroacetic acid (TCA) was added thereto so as to obtain a final concentration of 10% w/v. The mixture was allowed to stand still for 2 hours at 4° C., then centrifugation was performed at 11,000×g for 30 minutes. A supernatant was collected and combined with the same volume of 99% cold ethanol. The mixture was left to stand still overnight at 4° C.

Thereafter, the mixture was subjected to dialysis using a Spectra/Por Membrane (MW3500), and freeze-dried through a customary method, whereby 5 different freeze-dried culture supernatants (hereafter called 2085EPS, 2021EPS, 2001EPS, 2084EPS, and 2059EPS, corresponding to the above-mentioned strains) were obtained. These EPSs were individually dissolved in ultrapure water, and the pH was adjusted to 7 with NaOH. The thus-obtained 1% ultrapure water solutions were used in the following tests.

Example 1

Test 1: Skin Condition Test Using Hairless Mice

HOS:HR-1 hairless mice (female, 9 weeks old) were provided, and divided into 8 groups, each consisting of 6 animals, as shown below. The EPSs prepared in the above Production Example were applied to the mice in accordance with the test groups. Mice were irradiated with UV light onto the back from a UVB lamp (Vilber Lourmat, France) at a daily dose of 30 mJ/cm$^2$, and each EPS solution was applied thereto in an amount of 100 μL with a swab for 4 days. To the back of each mouse of the Control group, instead of a culture supernatant, the same volume of sterilized water was applied, and to that of the HA group, the same volume of aqueous 1% hyaluronic acid solution was applied.

In order to avoid any variation in UV dose in each group which might be caused by the presence of a residue of a sample applied on the day before, prior to UV irradiation, the back of each mouse was wiped with absorbent cotton wetted with sterilized water.

After the test, the surface of the skin was investigated as follows. Firstly, each mouse was fixed on a board, and opaque quick-drying silicone rubber (SILFLO, Flexico Developments) was applied onto the dorsal skin of the mouse, whereby a negative replica was obtained on a mount sheet. Subsequently, through customary methods, the negative replica was illuminated (epi-illumination) at an angle of 30 degrees, and the image was captured and input to a computer. After binarization, image analysis was performed, whereby area ratios were obtained. The results are shown in FIG. 1. As used herein, the term "area ratio" refers to the percentage of wrinkles present per unit skin area.

Test System
I: Control group (UV+, water)
II: HA group (UV+, 1% HA solution)
III: Strain 2059 group (UV+, 2059EPS)
IV: Strain 2021 group (UV+, 2021EPS)
V: Strain 2084 group (UV+, 2084EPS)
VI: Strain 2085 group (UV+, 2085EPS)
VII: Strain 2001 group (UV+, 2001EPS)
VIII: UV-group (UV-, water)

As is apparent from FIG. 1, when compared with the result from the Control group, in the groups in which lactic acid bacterium culture supernatants were employed (i.e., the EPS groups), effect of reducing UV-induced wrinkles was obtained. In contrast, in the group in which hyaluronic acid which has excellent skin moisturizing effect and which is a polysaccharide known to be produced by a lactic acid bacterium was employed, effect of inhibiting UV-induced wrinkle formation was not observed. This suggests that the active ingredient of the anti-wrinkle agent of the present invention is not hyaluronic acid.

Example 2

Test 2: Skin Condition Test Using Hairless Mice

Figure 2:
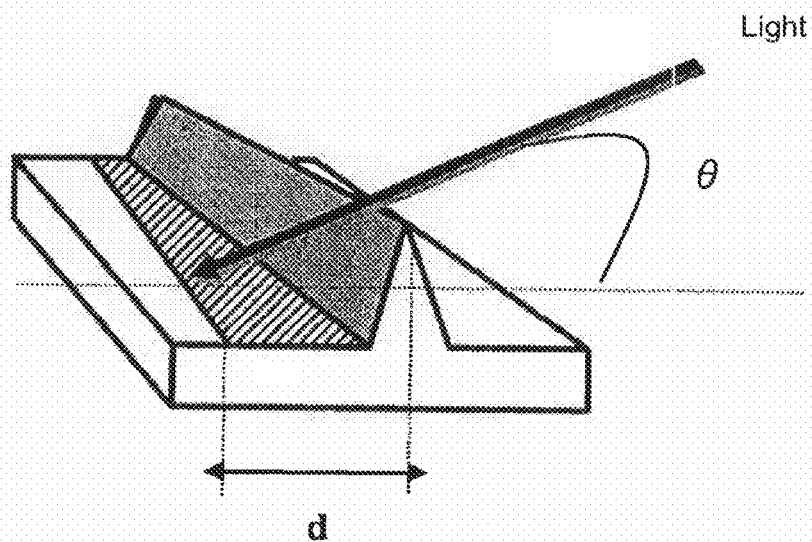
FIG. 2 is a diagram showing measurement of area ratios classified by wrinkle depth.

In order to further investigate the skin condition of hairless mice, area ratios classified by wrinkle depth were obtained for mice of the Control group, UV-group, and Strain 2085 group in Example 1. For this purpose, as shown in FIG. 2, wrinkle depth was defined by the product, d×tan θ, wherein d is the shadow length created by the epi-illumination. Then, for a portion that had been identified as a wrinkle by image processing in Example 1, area ratios were classified by the thus-determined wrinkle depth.

Figure 3:
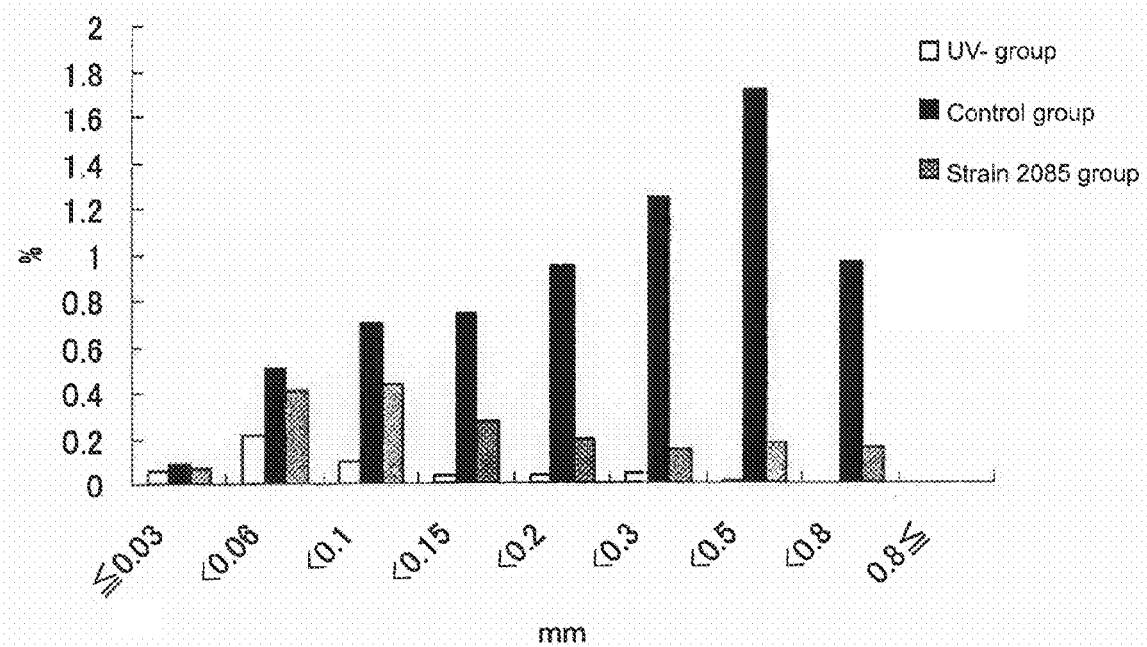
FIG. 3 shows the area ratios classified by wrinkle depth as measured in Example 2.
Figure 4:
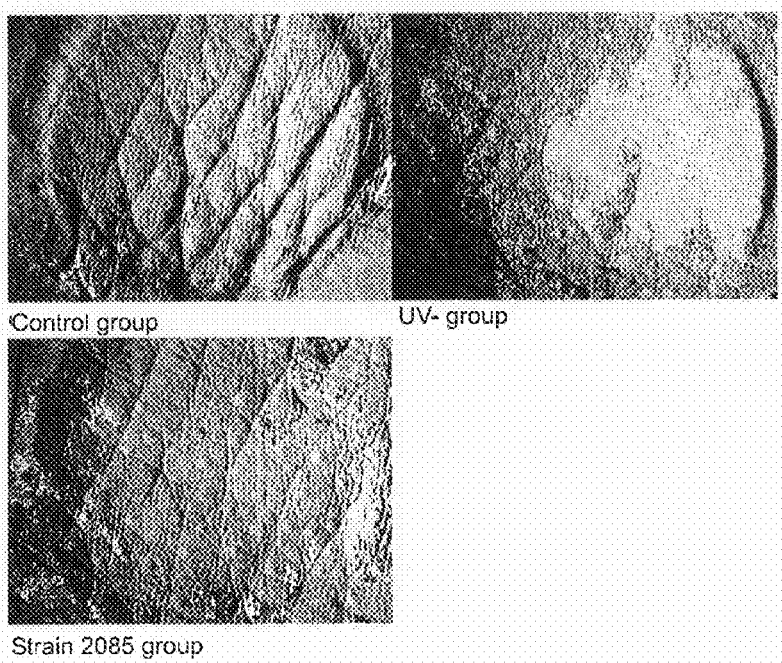
FIG. 4 shows photos of mouse dorsal skin replicas obtained in Example 2.

The results are shown in FIG. 3 along with photos of the mouse dorsal skin replicas (FIG. 4).

As is apparent from FIG. 3, whereas the Control group showed many deep wrinkles, the Strain 2085 group showed significantly suppressed formation of deep wrinkles. This tendency is also supported by FIG. 4.

Example 3

Production of a Lotion

A lotion having the following composition was produced. In production, (6) was dissolved in (7), and to the resultant solution, (1) to (5) were added and thoroughly stirred, to thereby give a lotion product.

TABLE 1

Composition

| | Material | Amount (wt. %) |
|---|---|---|
| 1 | Ethanol | 5.0 |
| 2 | 1,3-Butylene glycol | 2.0 |
| 3 | Polyoxyethylene hydrogenated castor oil | 0.05 |
| 4 | Methyl paraoxybenzoate | 0.1 |
| 5 | Perfume | 0.1 |
| 6 | 2085EPS | 0.2 |
| 7 | Distilled water | amount to make the total 100 |

Example 4

Production of an Emulsion

An emulsion having the following composition was produced. In production, (11) was combined with (7), (8), and (10), and the resultant mixture was heated. At 80° C., (1) to (6) were added and emulsified. Thereafter, (9) was added and stirred, then cooled to room temperature, to thereby give an emulsion product.

TABLE 2

Composition

| | Material | Amount (wt. %) |
|---|---|---|
| 1 | Stearic acid | 2.0 |
| 2 | Liquid paraffin | 5.0 |
| 3 | Squalane | 2.0 |
| 4 | Sorbitan monostearate | 0.05 |
| 5 | Polyoxyethylene(20) sorbitan monostearate | 2.0 |
| 6 | Butyl paraoxybenzoate | 0.05 |
| 7 | Glycerol | 2.0 |
| 8 | Methyl paraoxybenzoate | 0.1 |
| 9 | Perfume | 0.15 |
| 10 | 2085EPS | 0.03 |
| 11 | Distilled water | amount to make the total 100 |

Example 5

Production of a Cream

A cream having the following composition was produced. In production, (14) was combined with (9), (10), (12), and (13), and the resultant mixture was heated. At 80° C., (1) to (8) were added and emulsified. Thereafter, (11) was added and stirred, then cooled to room temperature, to thereby give a cream product.

TABLE 3

Composition

| | Material | Amount (wt. %) |
|---|---|---|
| 1 | Liquid paraffin | 23.0 |
| 2 | Petrolatum | 7.0 |
| 3 | Cetanol | 1.0 |
| 4 | Stearic acid | 2.0 |
| 5 | Beeswax | 2.0 |
| 6 | Sorbitan monostearate | 3.5 |
| 7 | Polyoxyethylene(20) sorbitan monostearate | 2.5 |
| 8 | Butyl paraoxybenzoate | 0.05 |
| 9 | 1,3-Butylene glycol | 1.0 |
| 10 | Methyl paraoxybenzoate | 0.1 |
| 11 | Perfume | 0.15 |
| 12 | Lactic acid bacterium culture liquid | 5.0 |
| 13 | 2085EPS | 0.1 |
| 14 | Distilled water | amount to make the total 100 |

INDUSTRIAL APPLICABILITY

The anti-wrinkle agent of the present invention which contains, as an active ingredient, a culture supernatant of a lactic acid bacterium belonging to *Streptococcus thermophilus* exhibits an excellent effect of inhibiting the formation of wrinkles. Also, since the anti-wrinkle agent contains, as an active ingredient, a culture supernatant produced by use of a natural lactic acid bacterium, it is very safe, and can be used as an ingredient of a variety of compositions for external use.

The invention claimed is:

1. An anti-wrinkle agent comprising, as an active ingredient, a culture supernatant containing at least one extracellular polysaccharide of a lactic acid bacterium belonging to *Streptococcus thermophilus*, wherein said *Streptococcus thermophilus* is at least one selected from the group consisting of *Streptococcus thermophiles* YIT2021 strain (FERM BP-7537), *Streptococcus thermophilus* YIT2001 strain (FERM BP-7538), *Streptococcus thermophilus* YIT2085 strain (FERM BP-10880), *Streptococcus thermophilus* YIT2084 strain (FERM BP-10879), and *Streptococcus thermophilus* YIT2059 strain (FERM BP-10878), and said agent is a skin anti-wrinkle agent.

2. A method for preventing formation of wrinkles induced by irradiation of skin with ultraviolet (UV) rays, comprising applying, to the skin, a composition comprising as an active ingredient a culture supernatant containing at least one extracellular polysaccharide of a lactic acid bacterium belonging to *Streptococcus thermophilus*, wherein said *Streptococcus thermophilus* is at least one selected from the group consisting of *Streptococcus thermophiles* YIT2021 strain (FERM BP-7537), *Streptococcus thermophilus* YIT2001 strain (FERM BP-7538), *Streptococcus thermophilus* YIT2085 strain (FERM BP-10880), *Streptococcus thermophilus* YIT2084 strain (FERM BP-10879), and *Streptococcus thermophilus* YIT2059 strain (FERM BP-10878).

3. The anti-wrinkle agent according to claim 1, wherein the lactic acid bacterium belonging to *Streptococcus thermophilus* is *Streptococcus thermophilus* YIT2021 strain (FERM BP-7537).

4. The anti-wrinkle agent according to claim 1, wherein the lactic acid bacterium belonging to *Streptococcus thermophilus* is *Streptococcus thermophilus* YIT2001 strain (FERM BP-7538).

5. The anti-wrinkle agent according to claim 1, wherein the lactic acid bacterium belonging to *Streptococcus thermophilus* is *Streptococcus thermophilus* YIT2085 strain (FERM BP-10880).

6. The anti-wrinkle agent according to claim 1, wherein the lactic acid bacterium belonging to *Streptococcus thermophilus* is *Streptococcus thermophilus* YIT2084 strain (FERM BP-10879).

7. The anti-wrinkle agent according to claim 1, wherein the lactic acid bacterium belonging to *Streptococcus thermophilus* is *Streptococcus thermophilus* YIT2059 strain (FERM BP-10878).

8. The anti-wrinkle agent according to claim 1, wherein the at least one extracellular polysaccharide contains at least one residue selected from the group consisting of glucose, galactose, N-acetylglucosamine and glucuronic acid.

* * * * *